United States Patent [19]

Hadley

[11] 4,409,225

[45] Oct. 11, 1983

[54] SUBSTITUTED BENZAMIDES

[75] Inventor: Michael S. Hadley, Sawbridgeworth, England

[73] Assignee: Beecham Group Limited, England

[21] Appl. No.: 243,762

[22] Filed: Mar. 16, 1981

[51] Int. Cl.³ .................. A61K 31/435; C07D 455/02
[52] U.S. Cl. ........................... 424/256; 260/239 BF; 546/93; 546/95; 546/112; 546/138
[58] Field of Search ......................... 546/138; 424/256

[56] References Cited

U.S. PATENT DOCUMENTS 4,213,983 7/1980 Hadley et al. ...................... 546/138

FOREIGN PATENT DOCUMENTS 2816884 11/1978 Fed. Rep. of Germany .
40-10418 5/1965 Japan .................................. 546/138

Primary Examiner—Ethel G. Love
Attorney, Agent, or Firm—Jacobs & Jacobs

[57] ABSTRACT

Compounds of formula (I) and pharmaceutically acceptable salts thereof:

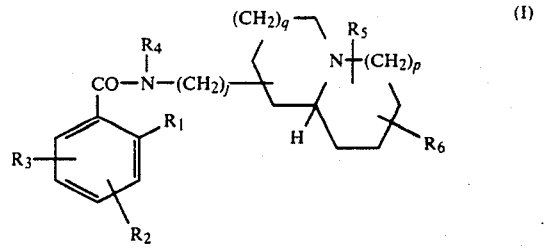

wherein:

$R_1$ is a $C_{1-6}$ alkoxy group;

$R_2$ and $R_3$ are the same or different and are hydrogen, halogen, $CF_3$, $C_{1-7}$ acyl, $C_{1-7}$ acylamino, $C_{1-6}$ alkyl-$S(O)_n$ wherein n is 0, 1 or 2, nitro, or amino, aminocarbonyl or aminosulphonyl optionally substituted by one or two $C_{1-6}$ alkyl groups;

or $R_1$ and $R_2$ taken together are methylendioxy or ethylenedioxy in which case $R_3$ is any one of the groups given for $R_1$ and $R_2$ above;

$R_4$ is hydrogen or $C_{1-6}$ alkyl;

$R_5$ is hydrogen, $C_{1-6}$ alkyl, phenyl or phenyl-$C_{1-6}$ alkyl, either of which phenyl moieties may be substituted by $C_{1-6}$ alkyl, $C_{1-6}$ alkoxy, $CF_3$ or halogen, and $R_6$ is hydrogen; or $R_5$ and $R_6$ are attached to two adjacent carbon atoms and form together with these two carbon atoms a fused benzene ring, which benzene ring may be substituted by $C_{1-6}$ alkyl, $C_{1-6}$ alkoxy, $CF_3$ or halogen; and j is 1 to 4; and p is 0 to 2 and q is 0 to 3, having useful pharmacological activity, a process for their preparation and their use.

8 Claims, No Drawings

SUBSTITUTED BENZAMIDES

This invention relates to novel substituted benzamides having useful pharmacological properties, to pharmaceutical compositions containing them, and to a process for their preparation.

West German Offenlegungsschrift No. 27 48 260.6 discloses that compounds of the formula (A), and their pharmaceutically acceptable salts:

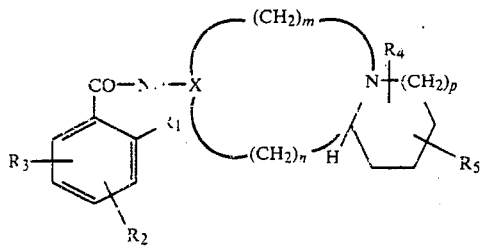

wherein:

$R_1$ is a $C_{1-6}$ alkoxy group;

$R_2$ and $R_3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-7}$ acyl amino, aminocarbonyl or aminosulphone optionally substituted by one or two $C_{1-6}$ alkyl groups, $C_{1-6}$ alkylsulphone or nitro groups;

X is either a nitrogen atom, in which case $m+n$ is 3 to 5, m is 2 to 4 and n is 1 to 3; or X is CH in which case $m+n$ is 2 to 5, m is 1 to 5, and n is 0 to 4;

p is 0 to 3;

$R_4$ is hydrogen, $C_{1-6}$ alkyl, phenyl or phenyl-$C_{1-6}$ alkyl, either of which phenyl moiety may be substituted by $C_{1-6}$ alkyl, $C_{1-6}$ alkoxy, $CF_3$ or halogen, and $R_5$ is hydrogen; or $R_4$ and $R_5$ are attached to two adjacent carbon atoms and form together with these two carbon atoms a fused benzene ring, which benzene ring may be substituted by $C_{1-6}$ alkyl, $C_{1-6}$ alkoxy, $CF_3$ or halogen; have useful pharmaceutical activity. For example it was disclosed that such compounds may be used for treatment of disorders of the gastro-intestinal function, such as retarded gastric emptying, dyspepsia, flatulence, oesophagal reflux, peptic ulcer and the like; and/or for the treatment of emesis.

It has now been found that a certain class of substituted benzamides structurally distinct from those compounds of the formula (A) also has useful pharmacological activity. For example the compounds have a stimulatory effect on gastric motility, and thus may be used in the treatment of disorders related to impaired gastrointestinal motility such as retarded gastric emptying, dyspepsia, flatulence, oesophagal reflux, peptic ulcer and emesis. The compounds also have a good therapeutic ratio based upon CNS effects.

Accordingly, the present invention provides a compound of the formula (I), and pharmaceutically acceptable salts thereof:

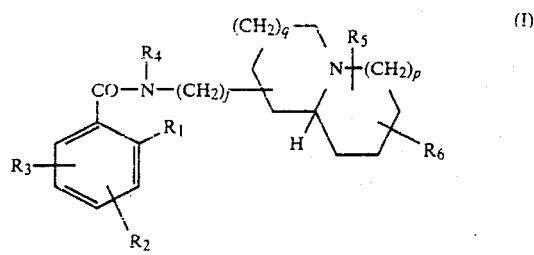

wherein:

$R_1$ is a $C_{1-6}$ alkoxy group;

$R_2$ and $R_3$ are the same or different and are hydrogen, halogen, $CF_3$, $C_{1-7}$ acyl, $C_{1-7}$ acylamino, $C_{1-6}$ alkyl-$S(O)_n$ wherein n is 0, 1 or 2, nitro, or amino, aminocarbonyl or aminosulphonyl optionally substituted by one or two $C_{1-6}$ alkyl groups;

or $R_1$ and $R_2$ taken together are methylendioxy or ethylenedioxy in which case $R_3$ is any one of the groups given for $R_1$ and $R_2$ above;

$R_4$ is hydrogen or $C_{1-6}$ alkyl;

$R_5$ is hydrogen, $C_{1-6}$ alkyl, phenyl or phenyl-$C_{1-6}$ alkyl, either of which phenyl moieties may be substituted by $C_{1-6}$ alkyl, $C_{1-6}$ alkoxy, $CF_3$ or halogen, and $R_6$ is hydrogen; or $R_5$ and $R_6$ are attached to two adjacent carbon atoms and form together with these two carbon atoms a fused benzene ring, which benzene ring may be substituted by $C_{1-6}$ alkyl, $C_{1-6}$ alkoxy, $CF_3$ or halogen; and j is 1 to 4; and p is 0 to 2 and q is 0 to 3.

Within formula (I) there is a group of compounds wherein $R_1$, $R_4$, $R_5$, $R_6$, j, q and p are as defined and $R_2$ and $R_3$ are the same or different and are hydrogen, halogen, $CF_3$, $C_{1-7}$ acyl, $C_{1-7}$ acylamino, $C_{1-6}$ alkylsulphonyl, nitro or amino, aminocarbonyl or aminosulphonyl optionally substituted by one or two $C_{1-6}$ alkyl groups.

Suitable examples of the group $R_1$ include methoxy, ethoxy and n- and iso-propoxy. Preferably $R_1$ is a methoxy group.

Suitable examples of the groups $R_2$ and $R_3$ include the following atoms and groups: hydrogen, chlorine, bromine, $CF_3$, formyl, acetyl, propionyl, n- and iso-butyryl, formylamino, acetylamino, propionylamino, n- and iso-butyrylamino, methyl, ethyl or and n- and iso-propyl-sulphone, nitro, amino, aminocarbonyl and aminosulphonyl and amino, aminocarbonyl, and aminosulphonyl substituted by one or two methyl, ethyl, n- or iso-propyl groups.

When $R_1$ and $R_2$ taken together are methylenedioxy or ethylenedioxy, they are most suitably ethylenedioxy.

Particularly suitable $R_2$ and $R_3$ groups include hydrogen, halogen, amino, and acylated amino as defined.

It is generally preferred that $R_2$ is in the 4-position relative to the carbonyl side chain for greater activity in the resultant compound of the formula (I). For the same reason it is generally preferred that $R_3$ is in the 5-position relative to the carbonyl side chain.

Particularly preferred $R_2$ groups include 4-amino and 4-(acylated amino) as defined. Preferably $R_2$ is 4-amino. Particularly preferred $R_3$ groups include 5-halo, such as 5-chloro.

Preferably the amide and side chain nitrogen atoms are separated by 2 or 3 carbon atoms.

Suitable examples of $R_4$ include hydrogen, methyl, ethyl, n- and iso-propyl, n-, sec- and tert-butyl, preferably hydrogen or methyl, in particular hydrogen Suitable examples of $R_5$ include hydrogen, methyl, ethyl, n- and iso-propyl, n-, sec- and tert-butyl; phenyl, phenyl-methyl, phenylethyl, phenyl-n-propyl, phenyl-iso-propyl, phenyl-n-, sec- and tert-butyl, any of which phenyl moieties may be substituted by $C_{1-6}$ alkyl, $C_{1-6}$ alkoxy, $CF_3$ or halogen. Suitable examples of such optional phenyl substituents include methyl, ethyl, n- and iso-propyl, n-, sec- and tert-butyl; methoxy, ethoxy, n- and iso-propoxy; $CF_3$, fluoro, chloro and bromo.

Preferred examples of $R_5$ include hydrogen; methyl, phenyl and benzyl. Often $R_5$ will substitute the carbon atom that is adjacent to the nitrogen atom in the ($R_5/R_6$ substituted) ring. Mostly such a $R_5$ group will be methyl.

When $R_5$ and $R_6$ represent a fused benzene ring, suitable optional substituents of that fused benzene ring include methyl, ethyl, n- and iso-propyl, n-, sec- and tert-butyl; methoxy, ethoxy and n- and iso-propoxy; $CF_3$, fluoro, chloro and bromo.

Suitably q is 0, 1 or 2, preferably 1.
Suitably p is 0, 1 or 2, preferably 1.
Often both p and q will be 1.

The pharmaceutically acceptable salts of the compound of the formula (I) include acid addition salts with conventional acids such as hydrochloric, hydrobromic, phosphoric, sulphuric, citric, tartaric, lactic and acetic acid and the like.

The pharmaceutically acceptable salts of the compounds of the formula (I) also include quaternary ammonium salts. Examples of such salts include such compounds quaternised by compounds such as $R_7$-Y wherein $R_7$ is $C_{1-6}$ alkyl, phenyl-$C_{1-6}$ alkyl or $C_{5-7}$ cycloalkyl, and Y is an anion of an acid. Suitable examples of $R_7$ include methyl, ethyl and n- and iso-propyl; and benzyl and phenylethyl. Suitable examples of Y include the halides such as chloride, bromide and iodide.

From the aforesaid it will be seen that favourably the moiety of formula (II):

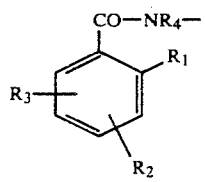

(II)

in a compound of the formula (I) will have the structure (III).

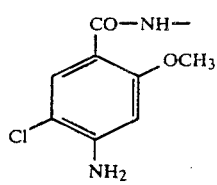

(III)

A suitable moiety of formula (II) may also be of formula (IV):

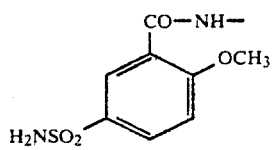

(IV)

Similarly, the moiety of formula (V):

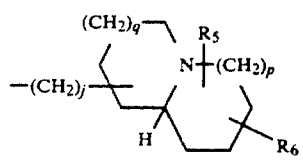

(V)

in a compound of formula (I) favourably has the structure (VI):

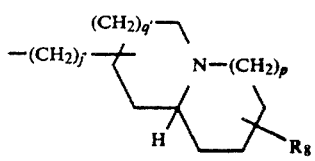

(VI)

wherein j' is 1 or 2; q' is 0 to 2, p is 0 to 2, and $R_8$ is hydrogen, $C_{1-6}$ alkyl, phenyl or phenyl-$C_{1-6}$-alkyl, either of which phenyl moieties may be substituted by $C_{1-6}$ alkyl, $C_{1-6}$ alkoxy, $CF_3$ or halogen.

Suitably q' is 0 or 1 and p is 0 or 1.
When p is 0 or 1, q' may also suitably be 2.
Preferably q' and p are both 1.

Suitable and preferred examples of $R_8$ include those listed hereinbefore for $R_5$. Often $R_8$ will substitute the carbon atom that is adjacent to the nitrogen atom in the ($R_8$ substituted) ring.

Particularly preferred examples of $R_8$ include hydrogen and methyl.

The moiety of formula (V), as defined, in a compound of formula (I) can also suitably have the structures (VII), (VIII) or (IX).

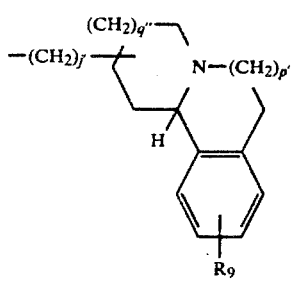

(VII)

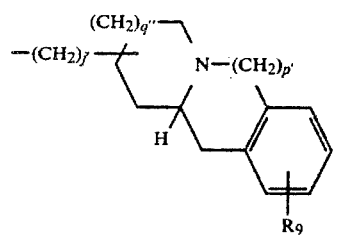

(VIII)

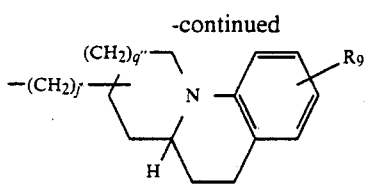

wherein q″ is 0 or 1, p′ is 0 or 1 and $R_9$ is hydrogen, $C_{1-6}$ alkyl, $C_{1-6}$ alkoxy, $CF_3$ or halogen, and j′ is as defined.

q″ and p′ are preferably 1.

Suitable examples of $R_9$ include hydrogen and the groups listed hereinbefore as suitable optional substituents for the fused benzene ring that can be formed by $R_5$ and $R_6$ and the carbon atoms to which they are attached in formula (I).

It will of course be realised that the compounds of the formula (I) have asymmetric centres, and thus are capable of existing in a number of stereoisomeric forms. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The invention also provides a process for the preparation of a compound of the formula (I), which process comprises reacting an acid of the formula (X):

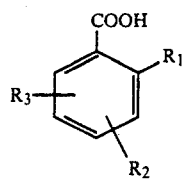

or a reactive derivative thereof, with a compound of formula (XI):

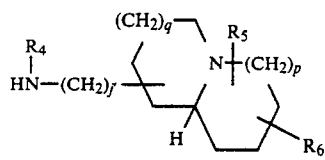

the variable groups being as defined in formula (I); and thereafter if desired or necessary converting a group $R_2$ or $R_3$ in the thus formed compound of the formula (I) to another group $R_2$ or $R_3$.

'Reactive derivative' when used herein means a derivative of the compound (X) which can be reacted with the compound (XI) to form an amido linkage between the acid group of the compound (X) and the amino group of the compound (XI).

Often this reactive derivative will be the acid halide, such as the acid chloride, of the acid (X). In such cases, the reaction will normally be carried out in an inert solvent, preferably in the presence of an acid acceptor. The inert solvent can be any solvent inert to both reactants, such as benzene, toluene, diethylether and the like. The acid acceptor is suitably an organic base such as a tertiary amine e.g. triethylamine, trimethylamine, pyridine or picoline, or an inorganic acid acceptor, such as calcium carbonate, sodium carbonate, potassium carbonate or the like. It should also be noted that it is possible to use certain acid acceptors as the inert solvent, for example organic bases.

Another useful reactive derivative of the acid (IX) that may be used is an acid ester, such as a methyl, ethyl, propyl or butyl ester, in which case the reaction is normally carried out by heating the reactants together in an inert solvent such as ethylene glycol.

The reaction may also be carried out by forming an anhydride of the acid (X) in the usual manner, and reacting that with the compound (XI); normally a conventional mixed anhydride will be used; or by reacting the acid (X) and the compound (XI) in the presence of a dehydrating catalyst such as a carbodiimide, for example dicyclohexyl carbodiimide.

The intermediates of the formulae (X) and (XI) are either known compounds or can be prepared by analogous processes to known compounds. Compounds of formula (X) for example may be synthesised from the corresponding ketone which is converted to a nitrile using p-toluene sulphonyl methyl isocyanate followed by reduction with a reducing agent such as lithium aluminium hydride.

The acid addition salts of compounds of the formula (I) may be prepared in entirely conventional manner by reacting a compound of the formula (I) in base form with the chosen acid.

The quaternary ammonium salts of the compounds of the formula (I) may be prepared in conventional manner for such salts, such as by reaction of the chosen compound of the formula (I) with a compound $R_7Y$ as defined. This reaction is suitably carried out in an appropriate solvent such as acetone, methanol, ethanol, dimethylformamide and the like, at ambient or raised temperature and pressure.

The interconversion of suitable groups $R_2$ and $R_3$ after formation of a compound of the formula (I) may be carried out by conventional methods. By way of example, nitro groups may be reduced to amino groups in the normal manner, and acylamino groups may be converted to amino also by conventional methods. Also a compound of the formula (I) wherein $R_2$ or $R_3$ is halogen can be prepared by a conventional halogenation of the corresponding compound of the formula (I) wherein the said $R_2$ or $R_3$ is hydrogen. Accordingly it will be realised that compounds of the formula (I) containing an $R_2$ or $R_3$ group which is convertible to another $R_2$ or $R_3$ group are useful intermediates, and as such form an important aspect of the invention.

The compounds of the formula (I) have useful pharmaceutical properties The invention thereof also provides a pharmaceutical composition comprising a compound of the formula (I) or a pharmaceutically acceptable salt thereof, together with a pharmaceutically acceptable carrier. Such compositions may be adapted for oral or parenteral administration, and as such may be in the form of tablets, capsules, syrups, reconstitutable powders, injectable and infusable solutions or suspensions and the like; the compositions may also be in the form of suppositories and the like. Normally orally administrable compositions are preferred.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented in a dry product for reconstitution with water or other suitable vehicle before use. Such liquid preparations may contain conventional additives such as suspending agents, emulsifying agents, nonaqueous vehicles (which may include edible oils), preservatives, and if desired conventional flavouring or colouring agents, and the like.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the compound.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention further provides a method of treatment of maladies in humans comprising the administration of an effective amount of a compound of the formula (I) or a pharmaceutically acceptable salt thereof. The 'effective amount' will depend in the usual way on a number of factors such as the nature and severity of the malady to be treated, and the actual compound used. Usually we have found that a dose of 0.1 to 50 mg/kg per day is quite sufficient to achieve a satisfactory treatment.

By way of illustration, unit doses will suitably contain 0.1 to 20 mg of the compound of formula (I), for example 0.5 to 10 mgs, administered 2 to 6 times per day.

Compounds of the formula (I) have the ability to potentiate the effect of conventional analgesics in migraine treatment when administered concurrently with the analgesic.

Thus the invention provides a pharmaceutical composition comprising a compound of the formula (I) and an analgesic.

The compound of the formula (I) and the analgesic, such as aspirin or paracetamol, will be present in the composition in amounts generally similar to their usual effective dose.

The composition can be a combination product, for example a tablet or capsule containing both a compound of the formula (I) and an analgesic for oral administration, or a twin pack comprising the two active ingredients made up for separate administration.

The invention accordingly provides a method of treatment of migraine comprising the administration to the sufferer of a compound of the formula (I) and an analgesic.

The following Examples illustrate the invention:

EXAMPLE 1

(±) 4-Acetylamino-5-chloro-2-methoxy-N(3′-quinolizidinyl-methyl)-benzamide (1)

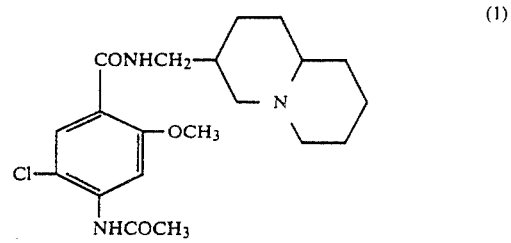

4-Acetylamino-5-chloro-2-methoxy-benzoic acid (2.2 g) was heated at 50° with thionyl chloride (20 ml) for 30 minutes. The solvent was evaporated, toluene was added and re-evaporated. The crude acid chloride was dissolved in toluene (70 ml), and triethylamine (5 ml) was added, followed by 3-aminomethylquinolizidine (1.4 g). After 30 minutes, dilute sodium hydroxide (10%, 5 ml) was added, and the mixture extracted with ethyl acetate (3×100 ml). The organic extracts were combined, dried and evaporated to give an oily residue. Chromatography on neutral alumina (100 g, 5% deactivated with water) eluting with ethyl acetate afforded one of the isomers (A, 1.2 g, 37%) of (±) 4-acetylamino-5-chloro-2-methoxy-N(3′-quinolizidinyl-methyl)-benzamide as a gum. Later fractions consisted of a mixture from which the second isomer (B, 0.5 g, 15%) of (±) 4-acetylamino-5-chloro-2-methoxy-N-(3′-quinolizidinyl-methyl)-benzamide, m.p. 174°–6° crystallised.

EXAMPLE 2

(±) 4-Amino-5-chloro-2-methoxy-N-(3′-quinolizidinyl-methyl)-benzamide (2)

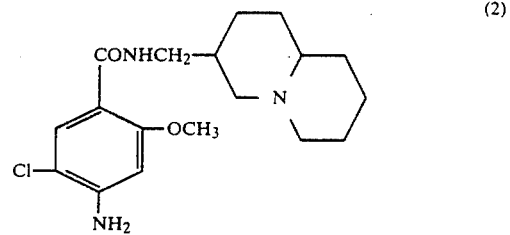

Isomer A (1.2 g) of (±) 4-acetylamino-5-chloro-2-methoxy-N-(3-quinolizidinyl-methyl)-benzamide was heated at reflux with potassium hydroxide (0.5 g) in ethanol (10 ml) and water (2 ml) for 3 hours. Solvent was evaporated and the residue dissolved in ethyl acetate and water.

The ethyl acetate extracts were combined, dried and evaporated to give, after recrystallisation from ethyl acetate/light petroleum, one of the isomers (A, 0.81 g, 76%) of 4-amino-5-chloro-2-methoxy-N-(3′-quinolizidinyl-methyl)-benzamide, m.p. 167°–8°.

Similarly, hydrolysis of isomer B (0.5 g) of (±) 4-acetylamino-5-chloro-2-methoxy-N-(3′-quinolizidinyl-methyl)-benzamide gave one of the isomers (B, 0.35 g, 78%) of (±) 4-amino-5-chloro-2-methoxy-N-(3′-quinolizidinyl-methyl)-benzamide, m.p. 209°–11°.

All spectra were recorded in deuterochloroform as solvent unless otherwise stated and chemical shifts are quoted in τ units.

EXAMPLE 1

Isomer A:
1.74 (1H, s, aromatic H), 1.84 (1H, s, aromatic H), 1.95–2.30 (2H, broad m, CONH and NHCOCH₃), 6.03 (3H, s, OCH₃), 6.15–6.50 (2H, m, NHCH₂), 7.1–9.0 (19H, m, remaining H including 3H singlet at 7.73 for NHCOCH₃).

Isomer B:
1.74 (1H, s, aromatic H), 1.84 (1H, s, aromatic H), 2.08–2.42 (2H, broad m, CONH and NHCOCH₃), 6.03 (3H, s, OCH₃), 6.55–6.80 (2H, m, NHCH₂), 7.0–9.0 (19H, m, remaining H including 3H singlet at 7.75 for NHCOCH₃).

EXAMPLE 2

Isomer A:
1.92 (1H, s, aromatic 6H), 2.07–2.40 (1H, broad m, CONH), 3.70 (1H, s, aromatic 3H), 5.54 (2H, s, NH₂), 6.13 (3H, s, OCH₃), 6.20–6.57 (2H, m, NHCH₂), 7.1–9.0 (16H, remaining -H).

Isomer B:
1.95 (1H, s, aromatic 6H), 2.2–2.45 (1H, broad m, CONH), 3.73 (1H, s, aromatic 3H), 5.53 (2H, s, NH₂), 6.15 (3H, s, OCH₃), 6.55–6.85 (2H, m, NHCH₂), 7.05–9.1 (16H, m, remaining H).

EXAMPLES 3 TO 12

The following compounds 3, 5, 7, 9 and 11 were prepared in a similar manner to Example 1 and compounds 4, 6, 8, 10 and 12 were prepared in a similar manner to Example 2.

EXAMPLE 3

(±)
4-Acetamido-5-chloro-2-methoxy-N-(1'-quinolizidinyl-methyl)-benzamide (3)

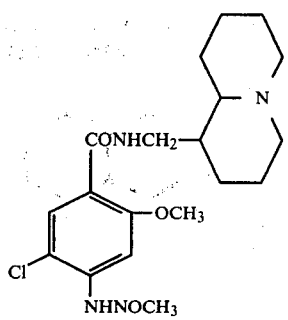
(3)

Trituration of the crude oil product with ether:ethylacetate (4:1) gave a solid which was separated and discarded. Evaporation of the mother liquors gave an oil which consisted of a mixture of isomers of the title compound (4.0 g, 70%).

EXAMPLE 4

(±)
4-Amino-5-chloro-2-methoxy-N-(1'-quinolizidinyl-methyl)-benzamide (4)

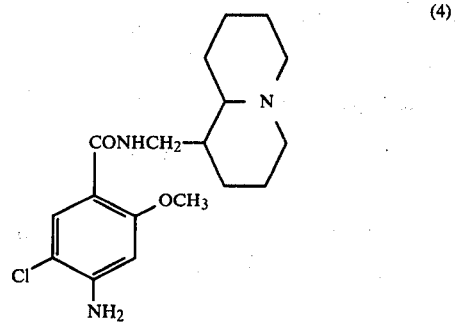
(4)

Following the procedures outlined in Example (2), the isomer mixture of (±) 4-acetamido-5-chloro-2-methoxy-N-(1'-quinolizidinyl-methyl)-benzamide (4.0 g) was converted to the crude product. Chromatography on Brockman II basic alumina (200 g), using methylene chloride as eluant, afforded one of the isomers (A, 0.9 g, 15%) of (±) 4-amino-5-chloro-2-methoxy-N-(1'-quinolizidinyl-methyl)-benzamide mp 155°–6°.

Elution with chloroform gave a mixture from which a solid was obtained, mainly isomer B (1.0 g, 20%) of (±) 4-amino-5-chloro-2-methoxy-N-(1'-quinolizidinyl-methyl)-benzamide mp 118°–25°.

Isomer A
1.91 (1H, s, aromatic 6H)
2.0–2.45 (1H, broad m, CONH)
3.63 (1H, s, aromatic 3H)
5.2–5.5 (2H, broad s, NH₂)
6.09 (3H, s, OCH₃)
6.2–6.75 (3H, m, NHCH₂ and >N-CH<)
7.0–9.0 (15H, remaining -H)

Isomer B (contains some Isomer A)
1.91 (1H, s, aromatic 6H)
1.8–2.5 (1H, broad m, CONH)
3.63, 3.66 (1H,2-s, aromatic 3H)
5.3–5.6 (2H, broad s, NH₂)
6.09, 6.14 (3H, 2-s, OCH₃)
6.05–6.8 (3H, m, NHCH₂ and >N-CH<)
7.0–9.0 (15H, remaining -H)

EXAMPLE 5

(±)
4-Acetamido-5-chloro-2-methoxy-N-β-(4'-quinolizidinyl-ethyl)benzamide (5)

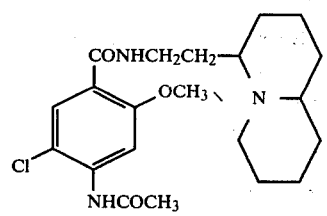
(5)

The title compound was isolated as a mixture of isomers (7.6 g, 40%) mp 174°–5° C.
1.80 (1H, s, aromatic H)
1.92 (1H, s, aromatic H)

1.9-2.2 (2H, broad s, CONH and NHCOCH₃)
6.03 (3H, s, OCH₃)
6.3-6.8 (4H, m, NHCH₂-, =N-CH= and

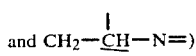

and CH₂—CH—N=)

7.5-9.0 (20H, m, remaining H including 3H singlet at 7.73 for NHCOCH₃)

EXAMPLE 6

(±)
4-Amino-5-chloro-2-methoxy-N-β-(4'-quinolizidinyl-ethyl)benzamide (6)

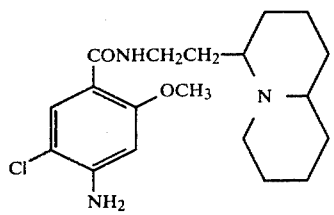

(6)

The title compound was isolated as a mixture of isomers (3.2 g, 50%) mp 140°-4° C.
1.92 (1H, s, aromatic 6H)
2.1-2.5 (1H, m, CONH-)
3.67 (1H, s, aromatic 3H)
5.2-5.5 (2H, m, NH₂)
6.15 (3H, s, OCH₃)
6.2-6.9 (4H, m, NHCH₂- =N-CH= and -CH₂-CH-N=)
7.6-9.0 (16H, m, remaining H)

EXAMPLE 7

(±)
4-Acetamido-5-chloro-2-methoxy-N-[3'-(1'-azabicyclo[5,4,0]-hendecyl-methyl)]-benzamide (7)

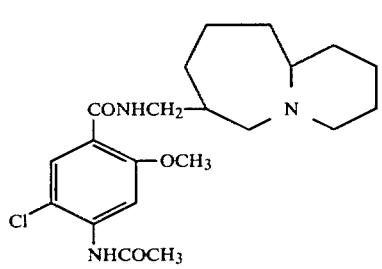

(7)

The title compound was prepared as a mixture of isomers (6.0 g, 75%) and was isolated as an oil.
1.78 (1H, s, aromatic H)
1.89 (1H, s, aromatic H)
1.7-2.3 (2H, m, CONH and NHCOCH₃)
6.13 (3H, s, OCH₃)
6.1-6.8 (m, 3H, NHCH₂CH= and =N-CH<)
7.0-9.0 (m, 20H, remaining H including 3H singlet at 7.73 for NHCOCH₃)

EXAMPLE 8

(±)
4-Amino-5-chloro-2-methoxy-N-[3'-(1'-azabicyclo[5,4,0]-hendecyl-methyl)]-benzamide (8)

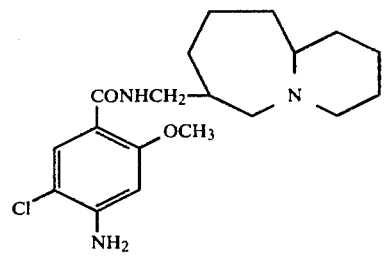

(8)

The title compound was prepared as a mixture of isomers (2.5 g, 60%) mp 136°-40° C.
1.94 (1H, s, aromatic 6H)
2.1-2.5 (1H, m, CONH)
3.68 (1H, s, aromatic 3H)
5.2-5.5 (2H, m, NH₂)
6.15 (3H, s, OCH₃)
6.4-7.0 (3H, m, NHCH₂CH= and =N-CH<)
7.1-9.0 (17H, m, remaining -H)

EXAMPLE 9

(±)
4-Acetamido-5-chloro-2-methoxy-N-(6'-methyl-3'-quinolizidinyl-methyl)-benzamide (9)

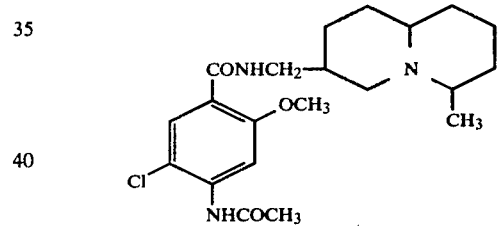

(9)

The title compound was prepared as a mixture of isomers (5.0 g, 45%) mp 147°-50° C.

EXAMPLE 10

(±)
4-Amino-5-chloro-2-methoxy-N-(6'-methyl-3'-quinolizidinyl-methyl-benzamide (10)

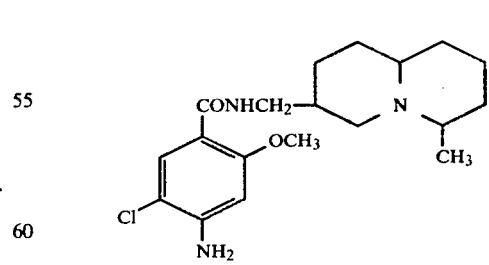

(10)

The title compound was prepared as a mixture of isomers (2.9 g, 70%) mp 134°-7° C.
(d⁶DMSO)
2.0-2.4 (1H, m, CONH)
2.31 (1H, s, aromatic 6H)
3.51 (1H, s, aromatic 3H)

4.0–4.3 (2H, m, N$\underline{H}$₂)

6.19 (3H, s, -OC$\underline{H}$₃)

6.1–7.3 (4H, m, NHC$\underline{H}$₂—, =N—C$\underline{H}$⟨, =N—$\underline{C}$H—CH₃)

8.0–9.2 (18H, m, remaining -$\underline{H}$ including 3H doubled at 9.03, J=6 Hz, CH-$\underline{C}$H₃).

EXAMPLE 11

(±)
4-Acetamido-5-chloro-2-methoxy-N-(2'-indolizidinyl-methyl)-benzamide (11)

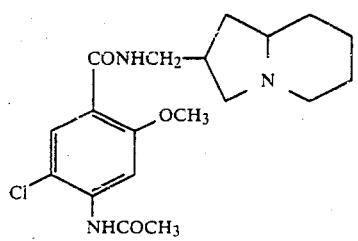
(11)

The title compound was prepared as a mixture of isomers (4.2 g, 90%) and was isolated as an oil.

EXAMPLE 12

(±)
4-Amino-5-chloro-2-methoxy-N-(2'-indolizidinyl-methyl)benzamide (12)

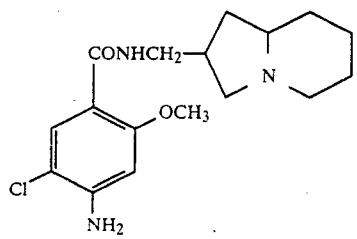
(12)

The title compound was prepared as a mixture of isomers (1.3 g, 35%) mp 159°–60° C.

1.93 (1H, s, aromatic 6$\underline{H}$)

1.8–2.1 (1H, m, CON$\underline{H}$)

3.70 (1H, s, aromatic 3$\underline{H}$)

5.4–5.7 (2H, m, N$\underline{H}$₂)

6.12 (3H, s, OC$\underline{H}$₃)

6.3–6.7 (2H, m, NHC$\underline{H}$₂-)

6.8–9.0 (14H, m, remaining $\underline{H}$)

EXAMPLE 13

(±)
4-Acetamido-5-chloro-2-methoxy-N-(3'-indolizidinyl-methyl)-benzamide (13)

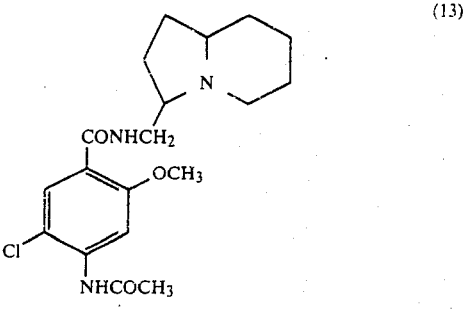
(13)

Following the procedures outlined in Example (1), the (±) 3-aminomethylindolizidine (3.0 g) was converted to the product as a mixture of isomers. Chromatography on Brookman II basic alumina (300 g), using methylene chloride/0.5% methanol as eluant, gave one of the isomers of (±) 4-acetamido-5-chloro-2-methoxy-N-(3'-indolizidinyl-methyl)-benzamide (A, 2.0 g, 27%) mp 121°–2°. Elution with methylene chloride/2.5% methanol gave the second isomer (B, 5.0 g, 67%) of (±) 4-acetamido-5-chloro-2-methoxy-N-(3'-indolizidinyl-methyl)-benzamide mp 108°–9° C.

Isomer A 1.87 (1H, s, aromatic $\underline{H}$)

1.90 (1H, s, aromatic $\underline{H}$)

1.6–2.1 (2H, m, CON$\underline{H}$- and NHCOCH₃)

6.07 (3H, s, OC$\underline{H}$₃)

6.0–9.0 (19H, remaining $\underline{H}$ including 3H singlet at 7.74 for NHCOC$\underline{H}$₃)

Isomer B 1.88 (1H, s, aromatic $\underline{H}$)

1.92 (1H, s, aromatic $\underline{H}$)

1.6–2.0 (2H, m, CON$\underline{H}$ and N$\underline{H}$COCH₃)

6.11 (3H, s, OC$\underline{H}$₃)

6.0–9.0 (19H, remaining $\underline{H}$ including 3H singlet at 7.74 for NHCOC$\underline{H}$₃)

EXAMPLE 14

(±)
4-Amino-5-chloro-2-methoxy-N-(3'-indolizidinyl-methyl)benzamide (14)

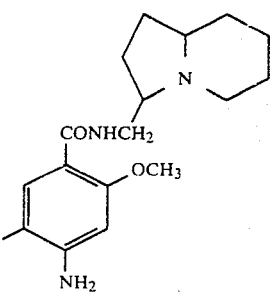
(14)

Following the procedures outlined in Example (2), Isomer A (2.0 g) of (±) 4-acetamido-5-chloro-2-methoxy-N-(3'-indolizidinylmethyl)-benzamide (13) was converted to one of the isomers (A, 1.3 g, 70%) of (±) 4-amino-5-chloro-2-methoxy-N-(3-indolizidinyl-methyl)benzamide, mp 164°-6°.

Similarly isomer B (5.0 g) of (±) 4-acetamido-5-chloro-2-methoxy-N-(3-indolizidinyl-methyl)-benzamide (13) was converted to one of the isomers (B, 2.5 g, 56%) of (±) 4-amino-5-chloro-2-methoxy-N-(3'-indolizidinyl-methyl)-benzamide, mp 169°-71° C.

Isomer A
1.89 (1H, s, aromatic 6H)
1.7-2.1 (1H, m, CONH)
3.70 (1H, s, aromatic 3H)
5.6-5.8 (2H, m, NH$_2$)
6.11 (3H, s, OCH$_3$)
6.05-9.00 (16H, m, remaining H)

Isomer B (d$^6$DMSO)
1.90 (1H, s, aromatic 6H)
1.9-2.25 (1H, s, CONH)
3.71 (1H, s, aromatic 3H)
5.4-5.8 (2H, m, NH$_2$)
6.14 (3H, s, OCH$_3$)
6.0-9.0 (16H, m, remaining H)

EXAMPLE 15

(±) 2-Methoxy-5-sulphamoyl-N-(3'-indolizidinylmethyl)-benzamide (15)

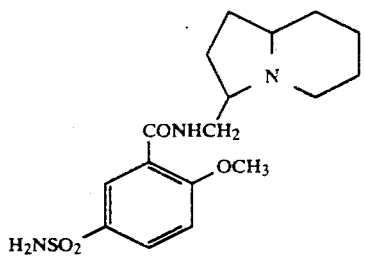

(15)

Ethyl chloroformate (1.3 g) was added, dropwise, to a cooled (0° C.) solution of 2-methoxy-5-sulphamoyl benzoic acid (2.8 g) and triethylamine (1.7 ml) in dry dimethylformamide (20 ml) and the solution was stirred at 0° C. for 30 minutes. A solution of (±) 3-aminomethylindolizidine (1.8 g) in dry dimethylformamide (5 ml) was added and the reaction mixture was stirred overnight. An excess of saturated sodium bicarbonate solution was added and the mixture was evaporated to dryness. Extraction with chloroform, drying (K$_2$CO$_3$) and concentration gave an oil. Column chromatography on neutral de-activated (10% water) alumina gave, on elution with chloroform, initially a mixture of isomers, followed on further elution, by one of the isomers (A, 0.9 g, 21%) or (±) 2-methoxy-5-sulphamoyl-N-(3'-indolizidinylmethyl)benzamide, mp 177°-9°.

Re-columning of the mixture, first on silica, eluting with 40% methanolic ethyl acetate and subsequently on 10% deactivated alumina eluting with chloroform gave the other isomer (B, 0.6 g, 14%) of (±) 2-methoxy-5-sulphamoyl-N-(3'-indolizidinyl-methyl)benzamide, mp 185°-6° C.

Isomer A (d$^6$DMSO)
1.6-1.9 (2H, m, CONH including 1H, d, at 8.21 J=2.4 Hz for aryl 6-H)
2.12 (1H, d,d, aryl 4-H J=2.4 Hz, 8.7 Hz)
2.6-2.85 (3H, m, SO$_2$NH$_2$ including 1H, d at 7.29 J=8.7 Hz for aryl 3-H)
6.05 (3H, s, OCH$_3$)
6.3-9.0 (remaining -H including d$^5$DMSO and HOD at 6.71)

Isomer B
1.6-1.85 (2H, m, CONH including 1H; d at 8.34 J=2.5 Hz for aryl 6-H)
2.09 (1H, d,d, aryl 4H J=2.5 Hz, 8.7 Hz)
2.5-2.85 (3H, m, SO$_2$NH$_2$ including 1H, d at 7.34, J=8.7 Hz for aryl 3H)
6.00 (3H, s, OCH$_3$)
6.2-9.0 (remaining -H including d$^5$DMSO and HOD at 6.69)

PHARMACOLOGICAL DATA—GASTRIC MOTILITY

Increase in Intragastric Pressure in the rat

The compounds of the Examples were tested for pharmacological activity in increasing intra-gastric pressure in the rat. Intragastric pressure changes were recorded from previously starved conscious and restrained rats using a fluid filled catheter inserted into the lumen of the stomach via a permanent gastric fistula. The catheter was connected to a physiological pressure transducer and pressure changes recorded on a hot wire pen recorder. In each animal a pre-dose period of 40 minutes was allowed to obtain a measure of spontaneous activity. An index of activity was obtained by measuring the average height of pressure waves during 10 minute periods. Values for 4 such periods were obtained during assessment of spontaneous activity and for the 40 minute period after the administration of the Compounds. Student "t" test was applied to the difference in average values obtained for spontaneous and post compound activity.

The minimum dose for activity is shown in Table 1.

TABLE 1

| Compound of Example No. | Dose mg/k | |
|---|---|---|
| | Subcut | oral |
| 2 (Isomer A) | 0.2 | 5.0 |
| 2 (Isomer B) | 5.0 | 5.0 |
| 14 (Isomer B) | 0.2 | |

CNS EFFECTS

Compounds were also tested for their ability to inhibit apomorphine induced stereotypy in rodents. Inactivity in these tests may be indicative of a low propensity to produce extra pyramidal side effects in man. The tests used were as follows.

Inhibition of apomorphine-induced biting in the rat

Apomorphine 5 mg/kg sc induces a stereotypic gnawing behaviour in rats which can be measured by a subjective scoring system; score 0—animal behaving normally; score 1—increased locomotion activity with occassional sniffing and licking; score 2—persistent licking of the bars of the cage with occasional biting; score 3—more sustained biting; score 4—intense biting at a particular part of the cage, animal no longer moving about.

Animals are individually placed in wire cages and after being allowed to become acclimatised are injected with apomorphine 5 mg/kg sc. Stereotypy is scored at 10 min intervals for 90 mins after apomorphine. Compounds are administered subcutaneously 15 minutes after the apomorphine. Compounds of Examples 2 (A and B), 4 (A and B), 8, 12 and 14 (A and B) were inactive in this test.

Inhibition of apomorphine-induced climbing in the mouse

This test is based on that described by Protain, P. et al (1976) Psychopharmacol. 50, 1-6.

Apomorphine 1 mg/kg sc induced mice to climb the wall of a wire cage (inverted food hopper—11×7.5×18 cm high). Mice acclimatised in their home cages in groups of 5 are placed under the hoppers immediately after the injection of apomorphine 1 mg/kg SC. At 10, 20 and 30 minutes after injection climbing behaviour scored. The mice are observed for 30 seconds and scored according to the position in which they spend the majority of time; score 0—four paws on floor of cage; score 1—2 paws only on walls; score 2—all four paws on wall of cage.

The scores at all 3 times for each mouse are summed for apomorphine only and for apomorphine plus compound groups of mice Inhibition of climbing is then calculated as follows.

% inhibition =

$$100 - 100 \left( \frac{\text{Total scores of drug treated group}}{\text{Total scores of apomorphine only group}} \right)$$

The Compound of Example 2 (Isomer A) was inactive in this test.
The Compound of Example 14 has an $ED_{50}$ of 20 mg/kg sc (Isomer A). 15 mg/kg sc (Isomer B).

Toxicity
No toxic effects were observed in the above tests.

I claim:

1. A compound of formula (I) and pharmaceutically acceptable salts thereof:

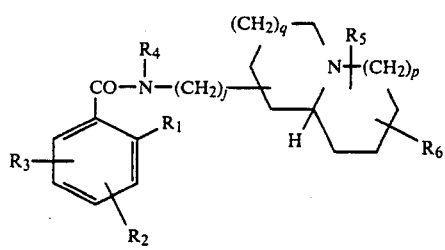

wherein:
$R_1$ is a $C_{1-6}$ alkoxy group;
$R_2$ and $R_3$ are the same or different and are hydrogen, halogen, $CF_3$, $C_{1-7}$ acyl, $C_{1-7}$ acylamino, $C_{1-6}$ alkyl-$S(O)_n$ wherein n is 0, 1 or 2, nitro, or amino, aminocarbonyl or aminosulphonyl optionally substituted by one or two $C_{1-6}$ alkyl groups;
or $R_1$ and $R_2$ taken together are methylendioxy or ethylenedioxy in which case $R_3$ is any one of the groups given for $R_1$ and $R_2$ above;
$R_4$ is hydrogen or $C_{1-6}$ alkyl;
$R_5$ is hydrogen, $C_{1-6}$ alkyl, phenyl or phenyl-$C_{1-6}$ alkyl, either of which phenyl moieties may be substituted by $C_{1-6}$ alkyl, $C_{1-6}$ alkoxy, $CF_3$ or halogen, and $R_6$ is hydrogen; and j is 1 to 4; and
p is 1 and q is 1.

2. A compound of formula (I) wherein the moiety of formula (II):

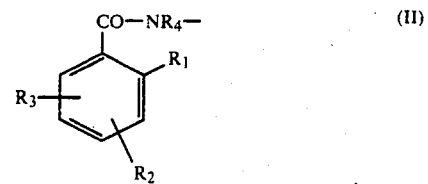

has the structure (III):

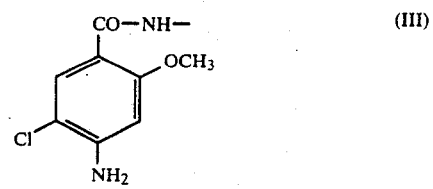

3. A compound according to claim 1 wherein the moiety of formula (V):

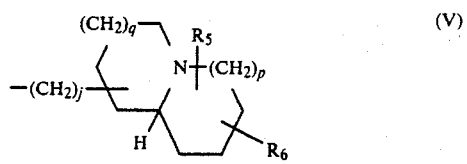

has the structure (VI):

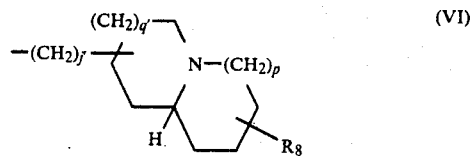

wherein j' is 1 or 2; q' is 1, p is 1, and $R_8$ is hydrogen, $C_{1-6}$ alkyl, phenyl or phenyl-$C_{1-6}$-alkyl, either of which phenyl moieties may be optionally substituted by $C_{1-6}$ alkyl, $C_{1-6}$ alkoxy, $CF_3$ or halogen.

4. A compound according to claim 3 wherein $R_8$ is hydrogen or methyl.

5. 4-Amino-5-chloro-2-methoxy-N-(3-quinolizidinylmethyl)benzamide.

6. Isomer A of 4-amino-5-chloro-2-methoxy-N-(3-quinolizidinylmethyl)-benzamide.

7. A pharmaceutical composition useful for treatment of disorders related to impaired gastric emptying, comprising a gastric emptying effective amount of a compound according to claim 1 and a pharmaceutically acceptable carrier.

8. A method of treating disorders related to impaired gastric emptying in humans and animals, which comprises administering to a human or animal in need thereof a gastric emptying effective amount of a compound according to claim 1.

* * * * *